United States Patent
Wagner

(10) Patent No.: US 9,068,080 B2
(45) Date of Patent: Jun. 30, 2015

(54) MEROCYANINE DERIVATIVES

(75) Inventor: Barbara Wagner, Lörrach (DE)

(73) Assignee: BASF SE, Ludwigshafen (DE)

( * ) Notice: Subject to any disclaimer, the term of this patent is extended or adjusted under 35 U.S.C. 154(b) by 1157 days.

(21) Appl. No.: 12/311,502

(22) PCT Filed: Oct. 5, 2007

(86) PCT No.: PCT/EP2007/060578
§ 371 (c)(1),
(2), (4) Date: Apr. 1, 2009

(87) PCT Pub. No.: WO2008/080645
PCT Pub. Date: Jul. 10, 2008

(65) Prior Publication Data
US 2010/0035839 A1 Feb. 11, 2010

(30) Foreign Application Priority Data

Oct. 13, 2006 (EP) .................................... 06122222

(51) Int. Cl.
| | | |
|---|---|---|
| A61K 31/695 | (2006.01) | |
| A61Q 90/00 | (2009.01) | |
| C07F 7/02 | (2006.01) | |
| C09B 23/01 | (2006.01) | |
| A61K 8/49 | (2006.01) | |
| A61K 8/58 | (2006.01) | |
| A61K 8/898 | (2006.01) | |
| A61Q 17/04 | (2006.01) | |
| C07F 7/08 | (2006.01) | |
| C09B 23/06 | (2006.01) | |
| C09B 23/10 | (2006.01) | |

(52) U.S. Cl.
CPC .............. *C09B 23/0066* (2013.01); *A61K 8/49* (2013.01); *A61K 8/4926* (2013.01); *A61K 8/494* (2013.01); *A61K 8/498* (2013.01); *A61K 8/585* (2013.01); *A61K 8/898* (2013.01); *A61Q 17/04* (2013.01); *C07F 7/0854* (2013.01); *C09B 23/0091* (2013.01); *C09B 23/06* (2013.01); *C09B 23/105* (2013.01)

(58) Field of Classification Search
CPC ....... A61K 8/49; A61K 8/4926; A61K 8/494; A61K 8/498; A61K 8/585; A61K 8/898; A61Q 17/04; C07F 7/0854; C09B 23/0066; C09B 23/0091; C09B 23/06; C09B 23/105
USPC ............. 514/63; 544/229; 549/214; 560/155; 558/303; 424/59, 70.9; 564/462
See application file for complete search history.

(56) References Cited

U.S. PATENT DOCUMENTS

| | | | |
|---|---|---|---|
| 4,283,488 A | 8/1981 | Van Lare | 430/588 |
| 4,749,643 A * | 6/1988 | Ohlschlager et al. | 430/512 |
| 5,380,700 A | 1/1995 | Miyazaki et al. | 504/239 |
| 5,806,834 A | 9/1998 | Yoshida | 252/589 |
| 5,939,465 A | 8/1999 | Kunita et al. | 522/31 |
| 6,358,496 B1 | 3/2002 | Zink et al. | 424/59 |
| 7,009,069 B2 | 3/2006 | Valla et al. | 560/171 |
| 7,407,648 B2 * | 8/2008 | Wagner et al. | 424/59 |
| 2005/0255055 A1 | 11/2005 | Wagner et al. | 424/59 |
| 2006/0204457 A1 | 9/2006 | Toda et al. | 424/59 |
| 2008/0124285 A1 | 5/2008 | Wagner et al. | 424/59 |
| 2008/0260661 A1 | 10/2008 | Kluijtmans et al. | 424/59 |
| 2008/0305058 A1 | 12/2008 | Richard | 424/60 |
| 2009/0010860 A1 | 1/2009 | Wagner et al. | 424/59 |

FOREIGN PATENT DOCUMENTS

| | | | |
|---|---|---|---|
| DE | WO2004/006878 | * | 1/2004 |
| DE | WO2006/003094 | * | 1/2006 |
| GB | 2433499 | | 6/2007 |
| WO | 2006/032741 | | 3/2006 |
| WO | 2007/014848 | | 2/2007 |

OTHER PUBLICATIONS

Corriu et al. Tetrahedron, 1992, 48(30), 6231-44.*
English language abstract for JP 9087630, Publication date: Mar. 31, 1997.

* cited by examiner

*Primary Examiner* — Kendra D Carter
(74) *Attorney, Agent, or Firm* — Shruti Costales

(57) ABSTRACT

Disclosed are merocyanine derivatives which correspond to the formula (I), wherein $L_1$, $L_2$ and $L_3$ independently of each other are hydrogen; or $L_1$ and $L_3$ may be linked together to form a carbocyclic ring; $R_3$ and $R_4$ independently of each other are CN; —$COR_5$; —$COOR_5$; —$CONR_5R_6$; $C_1$-$C_{22}$alkyl; $C_2$-$C_{22}$alkenyl; $C_2$-$C_{22}$alkinyl; $C_3$-$C_{12}$cycloalkyl; $C_3$-$C_{12}$cycloalkenyl; $C_7$-$C_{20}$aralkyl; $C_1$-$C_{20}$heteroalkyl; $C_3$-$C_{12}$cycloheteroalkyl; $C_3$-$C_{18}$heteroaralkyl; $C_6$-$C_{20}$ aryl; $C_1$-$C_{12}$alkylcarbonylamino-$C_6$-$C_{20}$aryl; $C_2$-$C_{12}$heteroaryl; or —$X_2$—$Sil_2$; n is a number from 1 to 4; the meaning of $R_1$ and $R_2$ depends on the definition of n. The compounds are useful as UV absorbers for cosmetic applications.

(I)

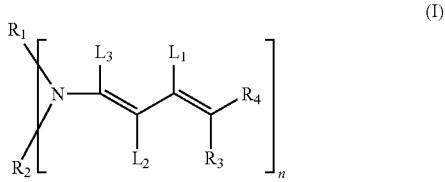

8 Claims, No Drawings

MEROCYANINE DERIVATIVES

The present invention relates to the use of merocyanine derivatives for protecting human and animal hair and skin from UV radiation and to cosmetic compositions comprising such compounds.

The compounds for use in accordance with the invention correspond to formula

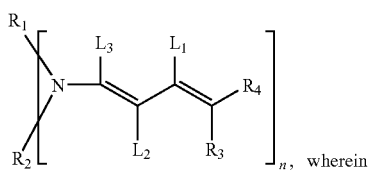

(1)

wherein $L_1$, $L_2$ and $L_3$ independently of each other are hydrogen; or $L_1$ and $L_3$ may be linked together to form a carbocyclic ring;

$R_3$ and $R_4$ independently of each other are CN; —$COR_5$; —$COOR_5$; —$CONR_5R_6$; $C_1$-$C_{22}$alkyl; $C_2$-$C_{22}$alkenyl; $C_2$-$C_{22}$alkynyl; $C_3$-$C_{12}$cycloalkyl; $C_3$-$C_{12}$cycloalkenyl; $C_7$-$C_{20}$aralkyl; $C_1$-$C_{20}$heteroalkyl; $C_3$-$C_{12}$cycloheteroalkyl; $C_3$-$C_{18}$heteroaralkyl; $C_6$-$C_{20}$aryl; $C_1$-$C_{12}$alkylcarbonylamino-$C_6$-$C_{20}$aryl; $C_2$-$C_{12}$heteroaryl; or —$X_2$—$Sil_2$;

n is a number from 1 to 4;

if n=1, $R_1$ and $R_2$ independently of each other are hydrogen; $C_1$-$C_{22}$alkyl; hydroxy-$C_1$-$C_{22}$alkyl; $C_2$-$C_{22}$alkenyl; $C_2$-$C_{22}$alkynyl; $C_3$-$C_{12}$cycloalkyl; $C_3$-$C_{12}$cycloalkenyl; $C_7$-$C_{20}$aralkyl; $C_1$-$C_{20}$heteroalkyl; $C_3$-$C_{12}$cycloheteroalkyl; $C_6$-$C_{20}$aryl; $C_3$-$C_{18}$heteroaralkyl; $C_2$-$C_{12}$heteroaryl; —$(CH_2)_n$—$SiR_8R_9R_{10}$; or —$X_1$—$Sil_1$;

if n=2, $R_1$ and $R_2$ are each $C_1$-$C_6$alkylene; or one of $R_1$ and $R_2$ is $C_1$-$C_6$alkylene and the other is as defined for n=1;

if n=3, one of $R_1$ and $R_2$ is a trivalent radical and the other is as defined as for n=1;

if n=4, one of $R_1$ and $R_2$ is a tetravalent radical and the other is as defined for n=1;

$R_5$ and $R_6$ independently of each other are hydrogen; $C_1$-$C_{22}$alkyl, $C_2$-$C_{22}$alkenyl, $C_2$-$C_{22}$alkynyl; $C_3$-$C_{12}$cycloalkyl; $C_3$-$C_{12}$cycloalkenyl; $C_7$-$C_{20}$aralkyl; $COR_7$; $C_1$-$C_{20}$heteroalkyl; $C_3$-$C_{12}$cycloheteroalkyl; $C_3$-$C_{18}$heteroaralkyl; $C_6$-$C_{20}$aryl; $C_1$-$C_5$alkoxy-$C_6$-$C_{20}$aryl; —$(CH_2)_t$—$SO_3H$; —$(CH_2)_v$—$(CO)$—$OR_7$; —$(CH_2)_t$—$O$—$C_6$-$C_{10}$aryl; $C_2$-$C_{12}$heteroaryl; —$(CH_2)_u$—$SiR_8R_9R_{10}$; or a radical —$X_2$—$Sil_2$;

$R_7$ is hydrogen; $C_1$-$C_{22}$alkyl; $C_2$-$C_{22}$alkenyl; $C_2$-$C_{22}$alkynyl; $C_3$-$C_{12}$cycloalkyl; $C_3$-$C_{12}$cycloalkenyl; $C_7$-$C_{20}$aralkyl; $C_1$-$C_{20}$heteroalkyl; $C_3$-$C_{12}$cycloheteroalkyl; $C_3$-$C_{18}$heteroaralkyl; $C_6$-$C_{20}$aryl; or $C_2$-$C_{12}$heteroaryl;

$R_8$, $R_9$, $R_{10}$ independently form each other are $C_1$-$C_{22}$alkyl; $C_6$-$C_{20}$aryl; $C_1$-$C_{22}$alkoxy; or O—$C_6$-$C_{20}$aryl;

or $L_3$ and $R_1$, $R_3$ and $R_4$, $R_1$ and $R_2$, $R_5$ and $R_6$ may be linked together to form 1, 2, 3 or 4 carbocyclic or N, O and/or S-heterocyclic rings, which may be further fused with other aromatic rings and each N in a N-heterocyclic ring may be unsubstituted or substituted by $R_{11}$;

and each alkyl, alkenyl, alkynyl, cycloalkyl or cycloalkylene group may be unsubstituted or substituted by one or more $R_{12}$;

and each aryl, heteroaryl, aralkyl, arylene, heteroarylene or aralkylene may be unsubstituted or substituted by one or more $R_{13}$;

$R_{11}$ is $R_{14}$; $COR_{14}$; $COOR_{14}$; or $CONR_{14}R_{15}$;

$R_{12}$ is halogen, OH; $NR_{16}R_{17}$; O—$R_{16}$; S—$R_{16}$; CO—$R_{16}$; O—CO—$R_{16}$; oxo; thiono; CN; $COOR_{16}$; $CONR_{16}R_{17}$; $SO_2NR_{16}R_{17}$; $SO_2R_{16}$; $SO_3R_{16}$; $SiR_8R_9R_{10}$; $OSiR_8R_9R_{10}$; $POR_8R_9$; or a radical —$X_3$—$Sil_3$;

$R_{13}$ is $C_1$-$C_{12}$alkylthio; $C_3$-$C_{12}$cycloalkylthio; $C_1$-$C_{12}$alkenylthio; $C_3$-$C_{12}$cycloalkenylthio; $C_1$-$C_{12}$alkoxy; $C_3$-$C_{12}$cycloalkoxy; $C_1$-$C_{12}$alkenyloxy; or $C_3$-$C_{12}$cycloalkenyloxy which may be unsubstituted or substituted by one or more $R_{12}$; halogen; CN; SH; OH; CHO; $R_{18}$; $OR_{18}$; $SR_{18}$; $C(R_{18})$=$CR_{19}R_{20}$; O—CO—$R_{19}$; $NR_{18}R_{19}$; $CONR_{18}R_{19}$; $SO_2NR_{18}R_{19}$; $SO_2R_{18}$; $COOR_{18}$; $OCOOR_{18}$; $NR_{19}COR_{20}$; $NR_{19}COOR_{20}$; $SiR_8R_9R_{10}$; $OSiR_8R_9R_{10}$; P(=O)$R_8R_9$; or a radical —$X_4$—$Sil_4$;

$R_{14}$, $R_{15}$, $R_{16}$, $R_{17}$, $R_{18}$, $R_{19}$ and $R_{20}$ independently of each other are hydrogen; $C_1$-$C_{22}$alkyl; $C_3$-$C_{12}$cycloalkyl; $C_2$-$C_{12}$alkenyl; $C_3$-$C_{12}$cycloalkenyl; $C_6$-$C_{20}$aryl; $C_2$-$C_{12}$heteroaryl; $C_7$-$C_{18}$aralkyl; or $C_3$-$C_{18}$heteroaralkyl;

$R_{14}$ and $R_{15}$, $R_{16}$ and $R_{17}$ and/or $R_{18}$ and $R_{19}$ may be linked together to form unsubstituted or $C_1$-$C_4$alkyl-substituted pyrrolidine, piperidine, piperazine or morpholine;

$X_1$, $X_2$, $X_3$ and $X_4$ independently from each other are a linker;

$Sil_1$, $Sil_2$, $Sil_3$ and $Sil_4$ independently from each other are a silane-, oligosiloxane or polysiloxane moiety;

t is a number from 0 to 12;

u is a number from 0 to 12; and v is a number from 0 to 12.

$Sil_1$, $Sil_2$, $Sil_3$ and $Sil_4$ independently from each other are an oligosiloxane moiety selected from $Si(R_8)_m[OSi(R_9)]_o$; wherein $R_8$ and $R_9$ independently form each other are $C_1$-$C_{22}$alkyl; $C_6$-$C_{20}$aryl; $C_1$-$C_{22}$alkoxy; or O—$C_6$-$C_{20}$aryl;

m is 0; 1; or 2, o is 3, 2 or 1; wherein the sum of m+n is 3.

Halogen is chloro, bromo, fluoro or iodo, preferably a fluoro, more preferably fluoro alkyl like trifluormethyl, α,α, α-trifluorethyl or perfluorinated alkyl groups like heptafluorpropyl.

Alkyl, cycloalkyl, alkenyl, alkylidene or cycloalkenyl residues can be straight-chain or branched, or also monocyclic or polycyclic.

Alkenyl is for example straight-chain $C_2$-$C_{12}$alkenyl or preferably branched $C_3$-$C_{12}$alkenyl.

$C_1$-$C_{22}$alkyl is for example methyl, ethyl, n-propyl, isopropyl, n-butyl, sec.-butyl, isobutyl, tert.-butyl, n-pentyl, 2-pentyl, 3-pentyl, 2,2-dimethylpropyl, n-hexyl, n-octyl, 1,1,3,3-tetramethylbutyl, 2-ethylhexyl, nonyl, decyl, n-octadecyl, eicosyl, oder dodecyl.

$C_3$-$C_{12}$cycloalkyl is for example cyclopropyl, cyclobutyl, cyclopentyl, cyclohexyl, trimethylcyclohexyl, menthyl, thujyl, bornyl, 1-adamantyl or 2-adamantyl.

$C_2$-$C_{12}$alkenyl or $C_3$-$C_{12}$cycloalkenyl refers to unsaturated hydrocarbon residues containing one or multiple double bonds such vinyl, allyl, 2-propen-2-yl, 2-buten-1-yl, 3-buten-1-yl, 1,3-butadiene-2-yl, 2-cyclobutene-1-yl, 2-pentene-1-yl, 3-pentene-2-yl, 2-methyl-1-butene-3-yl, 2-methyl-3-butene-2-yl, 3-methyl-2-butene-1-yl, 1,4-pentadiene-3-yl, 2-cyclopentene-1-yl, 2-cyclohexene-1-yl, 3-cyclohexene-1-yl, 2,4-cyclohexadiene-1-yl, 1-p-menthene-8-yl, 4(10)-thujene-10-yl, 2-norbornene-1-yl, 2,5-norbornadiene-1-yl, 7,7- dimethyl-2,4-norcaradiene-3-yl or different isomers selected from hexenyl, octenyl, nonenyl, decenyl or dodecenyl.

$C_7$-$C_{18}$aralkyl is for example benzyl, 2-benzyl-2-propyl, β-phenyl-ethyl, 9-fluorenyl, α,α-dimethylbenzyl, ω-phenyl-butyl, ωphenyl-octyl, ω-phenyl-dodecyl or 3-methyl-5-(1',1',3',3'-tetramethyl-butyl)-benzyl.

The $C_7$-$C_{18}$aralkyl moiety may be unsubstituted or substituted on the alkyl- as well at the aryl-moiety of the aralkyl-group, but preferably is substituted on the aryl-moiety.

($C_1$-$C_6$)alkylidene is for example methylene, ethyl-1-ene or propyl-2-ene.

$C_6$-$C_{20}$aryl is for example phenyl, naphthyl, biphenylyl, 2-fluorenyl, phenanthryl, anthracenyl or terphenylyl.

$C_2$-$C_{12}$heteroaryl is for example an unsaturated or aromatic radical with 4n+2 conjugated π-electrons, such as 2-thienyl, 2-furyl, 2-pyridyl, 2-thiazolyl, 2-oxazolyl, 2-imidazolyl, isothiazolyl, triazolyl or any other ringsystem consisting of thiophene-, furan-, pyridine, thiazol, oxazol, imidazol, isothiazol, triazol, pyridine- and phenyl rings, which are unsubstituted or substituted by 1 to 6 ethyl, methyl, ethylene and/or methylene groups, such as benzotriazolyl.

$C_3$-$C_{18}$heteroaralkyl is for example a $C_1$-$C_8$ alkyl moiety which is substituted by a $C_2$-$C_{12}$heteroaryl group.

If $Sil_1$, $Sil_2$ $Sil_3$ and $Sil_4$ are an oligosiloxane radical, it is preferably selected from a group of formula

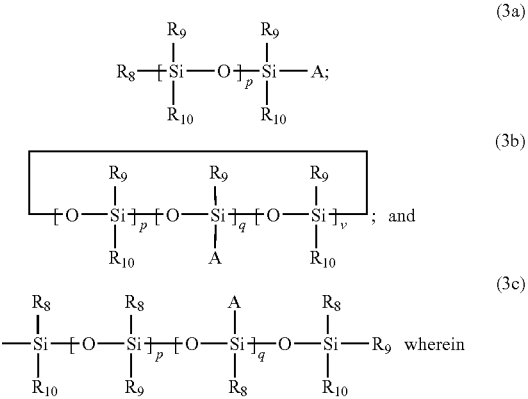

A is a bond to the linker $X_1$; $x_2$, $x_3$ and/or $X_4$;
$R_8$, $R_9$, $R_{10}$ independently form each other are $C_1$-$C_{22}$alkyl; $C_6$-$C_{20}$aryl; $C_1$-$C_{22}$alkoxy; or O—$C_6$-$C_{20}$aryl;
p is a number from 0 to 10;
q is a number from 1 to 10; and
v is a number from 0 to 1.

If $Sil_1$, $Sil_2$ $Sil_3$ and $Sil_4$ are an polysiloxane radical, it is preferably selected from a group of formula

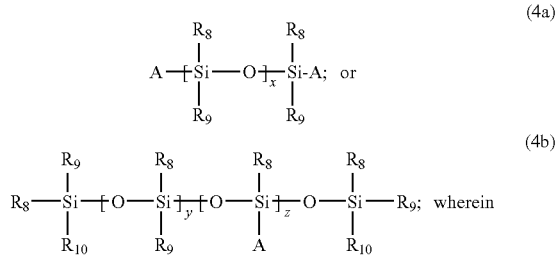

$R_8$, $R_9$, $R_{10}$ independently form each other are $C_1$-$C_{22}$alkyl; $C_6$-$C_{20}$aryl; $C_1$-$C_{22}$alkoxy; or O—$C_6$-$C_{20}$aryl;

A is a bond to the linker $X_1$ or $X_2$;
x is a number from 4 to 250;
y is a number from 5 to 250; and
z is a number from 1 to 50.

Preferred silane groups are trimethylsilane, triethylsilane, tripropylsilane, triisopropylsilane, dimethyl tert-butylsilane, dimethyl thexylsilane, triphenylsilane, dimethylphenylsilane and the like.

The linkers $X_1$, $X_2$, $X_3$ and $X_4$ are preferably a divalent radical of formula

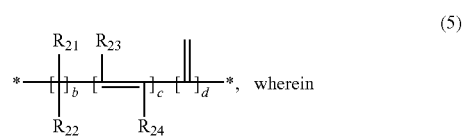

$R_{21}$, $R_{22}$, $R_{23}$ and $R_{24}$ independently form each other are hydrogen; $C_1$-$C_{22}$alkyl; $C_6$-$C_{20}$aryl; $C_1$-$C_{22}$alkoxy; or O—$C_6$-$C_{20}$aryl;
b is a number from 0 to 30;
c is a number from 0 to 6; and
d is a number from 0 to 1;

Preferably compounds of formula (1) are used, wherein $L_1$ and $L_3$ together form a bivalent radical selected from

$R_1$ and $R_2$ together form a bivalent radical selected from

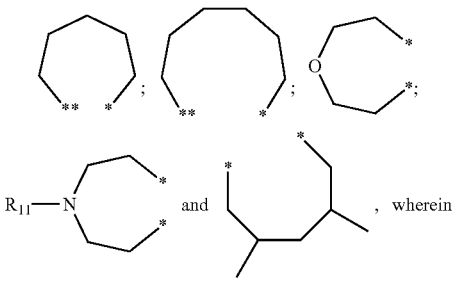

$R_{11}$ is defined as in formula (1).

$R_3$ and $R_4$ together form a carboyclic or heterocyclic biradical selected from

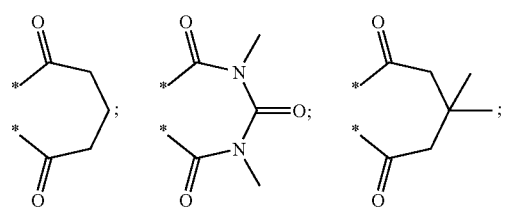

-continued

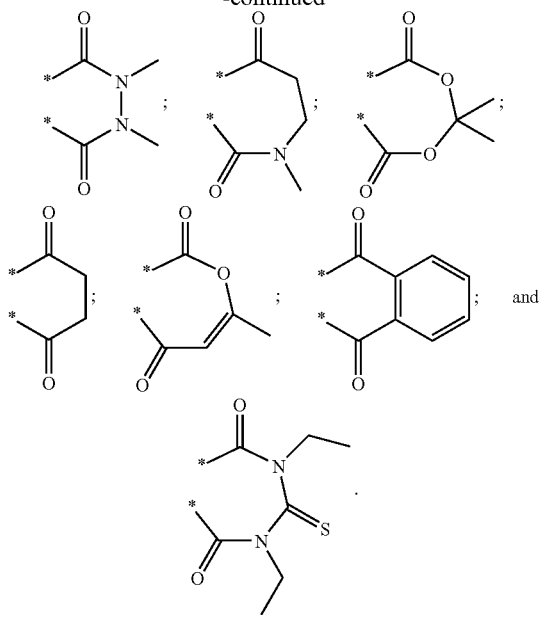

Preferred is also the use of compounds of formula (1), wherein
R$_1$ and L$_3$ form a bivalent radical selected from

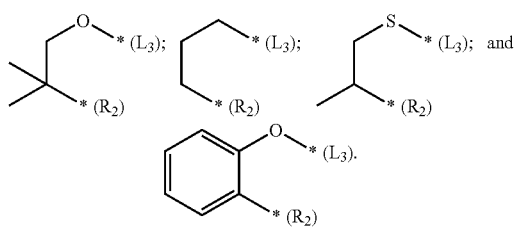

Preferably merocyanine derivatives are used in the present invention, wherein in formula (1)
R$_1$ is C$_1$-C$_8$alkyl; a radical X$_1$—Sil$_1$, wherein X$_1$ is C$_1$-C$_3$alkylene; and Sil$_1$ is a radical of formula

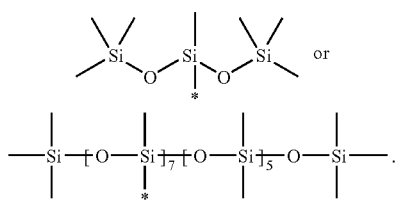

Furthermore, merocyanine derivatives are used, wherein in formula (1)
R$_1$ is a tetravalent radical of formula

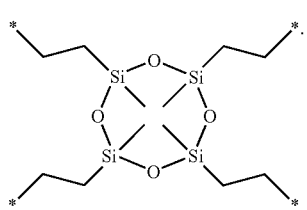

Most preferred merocyanine derivatives are those compounds, wherein in formula (1)
R$_2$ is hydrogen; or C$_1$-C$_3$alkyl; and
R$_1$, R$_3$, R$_4$, L$_1$, L$_2$, L$_3$ and n are defined as in formula (1).
Further preferred merocyanine derivatives are those compounds, wherein in formula (1)
R$_3$ is X$_2$—Sil$_2$, wherein Sil$_2$ is a radical of formula

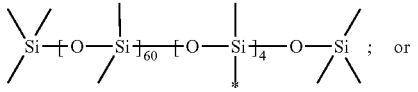

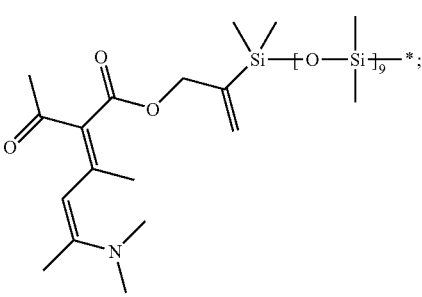

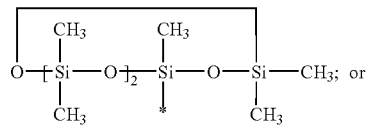

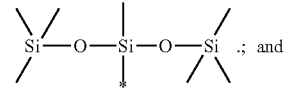

X$_2$ is C$_1$-C$_{18}$alkylene; or a bivalent radical of the formula

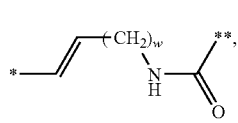 (5a)

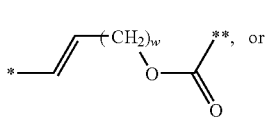 (5b)

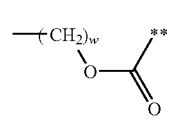 (5c)

wherein the asterix * is linked to Sil$_1$ or Sil$_2$ and the asterix ** is linked to R$_3$ or R$_4$; and
w is a number from 0 to 30.
Most preferred are also merocyanine derivatives, wherein in formula (1)
R$_4$ is —COOR$_5$; or C≡N;
R$_5$ is hydrogen; or C$_1$-C$_{22}$alkyl; and
R$_1$, R$_2$, R$_3$, L$_1$, L$_2$, L$_3$ and n are defined as in formula (1).

Very most preferred merocyanine derivatives correspond to formula

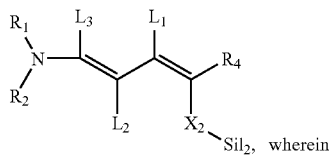, wherein $R_1$ and $R_2$ independently from each other are hydrogen; or $C_1$-$C_5$alkyl;

$L_1$, $L_2$ and $L_3$ are hydrogen; or $L_1$ and $L_3$ form a bivalent radical selected from

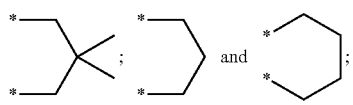

$R_4$ is —$COR_5$;
$R_5$ is $C_1$-$C_5$alkyl;
$Sil_2$ is a radical of formula

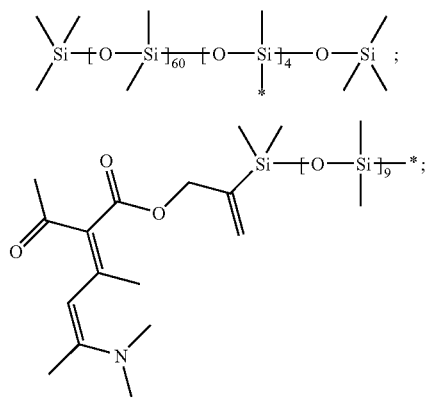

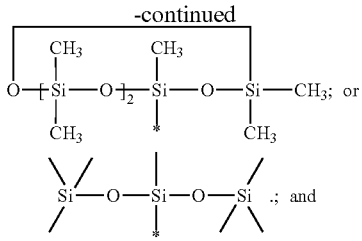

$X_2$ is $C_1$-$C_{18}$alkylene; or a bivalent radical of the formula (5a), (5b) or (5c).

Very most merocyanine derivatives correspond to formula (7)

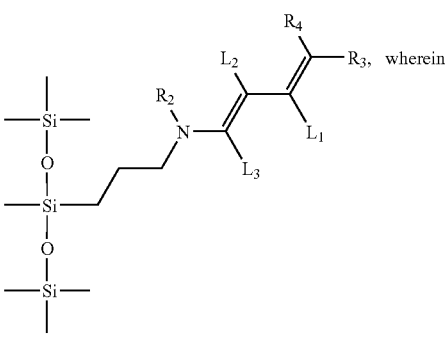

$R_2$ is hydrogen; or $C_1$-$C_3$alkyl;
$L_1$ and $L_3$ together form a bivalent radical selected from

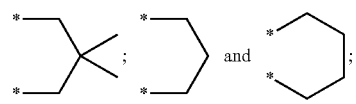

$R_3$ and $R_4$ independently from each other are CN; —$COR_5$; —$COOR_5$; or —$CONR_5R_6$; and
$R_5$ and $R_6$ independently of each other are hydrogen; or $C_1$-$C_{22}$alkyl; and
$L_2$ is defined as in formula (1).

Very most merocyanine derivatives correspond to formula

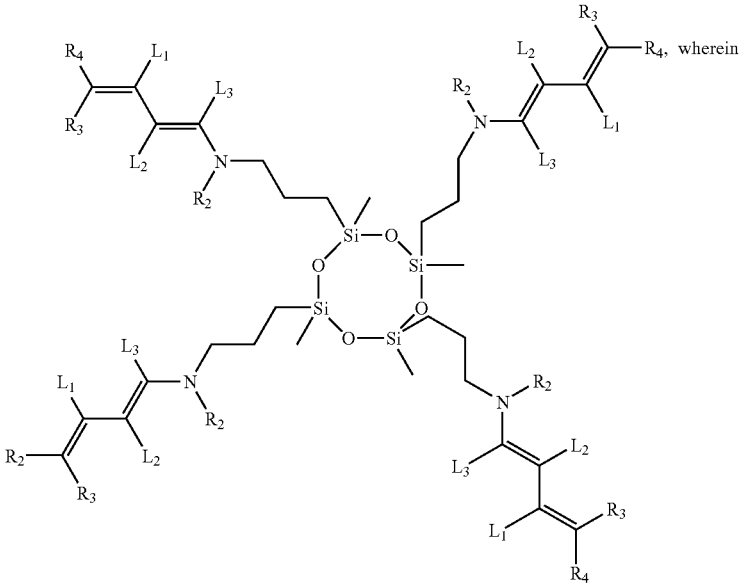, wherein $R_2$ is hydrogen; or $C_1$-$C_3$alkyl;

$R_3$ and $R_4$ independently from each other are CN; —COR$_5$; —COOR$_5$; or —CONR$_5$R$_6$;

$R_5$ and $R_6$ independently of each other are hydrogen; or $C_1$-$C_{22}$alkyl;

$L_1$, $L_2$ and $L_3$ are hydrogen; or $L_1$ and $L_3$ form a bivalent radical selected from

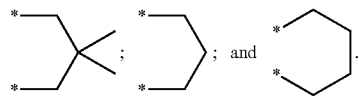

Examples of merocyanine derivatives which are useful for the present invention are listed in Table 1 below:

TABLE 1

MC 01

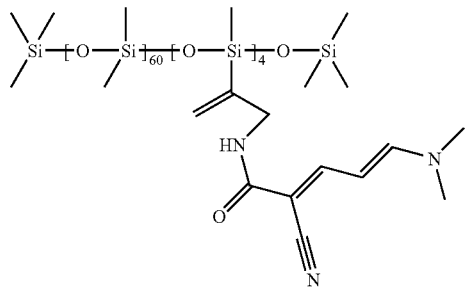

MC 02

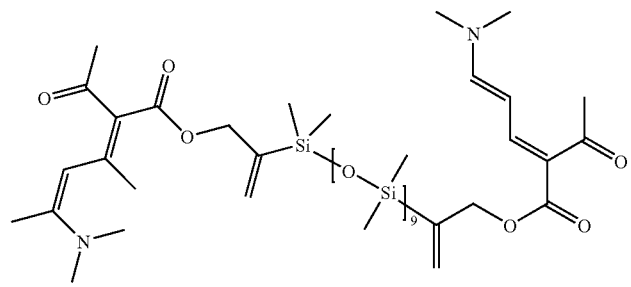

MC 03

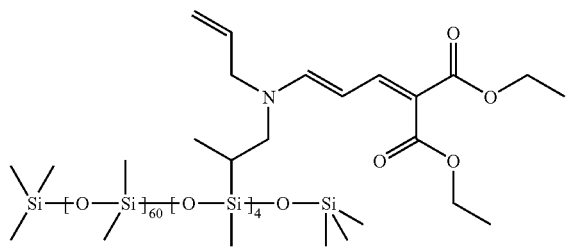

MC 04

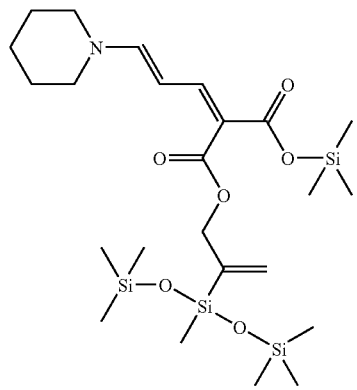 [SMILES: C=C(COC(=O)/C(=C\C=C\N1CCCCC1)C(=O)O[Si](C)(C)C)[Si](C)(O[Si](C)(C)C)O[Si](C)(C)C]

TABLE 1-continued
MC 05
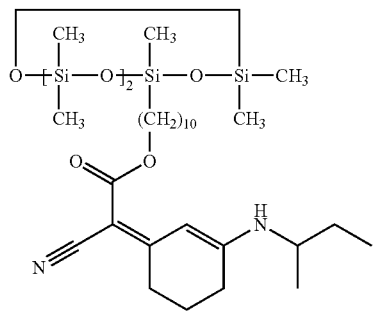
MC 06
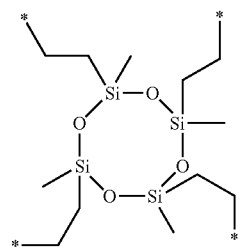 [SMILES: *CC[Si]1(C)O[Si](C)(CC*)O[Si](C)(CC*)O[Si](C)(CC*)O1]
MC 07
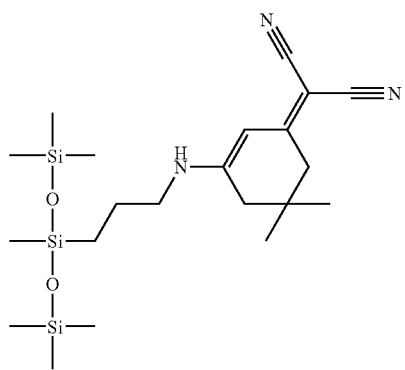 [SMILES: CC1(C)CC(NCCC[Si](C)(O[Si](C)(C)C)O[Si](C)(C)C)=CC(=C(C#N)C#N)C1]
MC 08
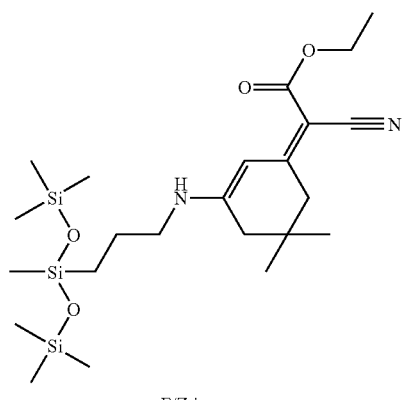
E/Z isomers TABLE 1-continued
MC 09
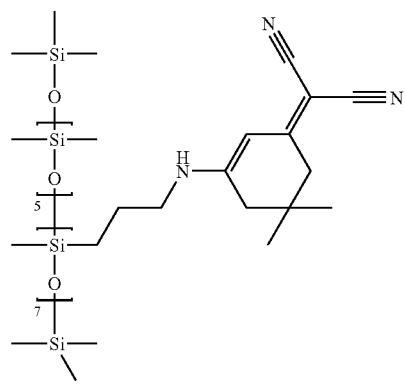
MC 10
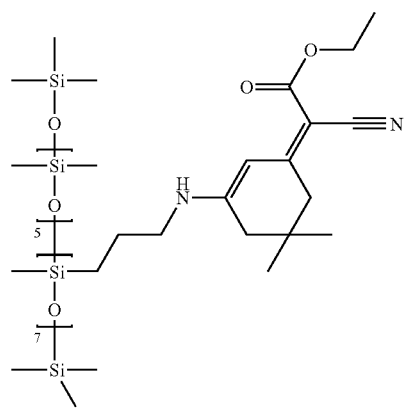
E/Z isomers
MC 11
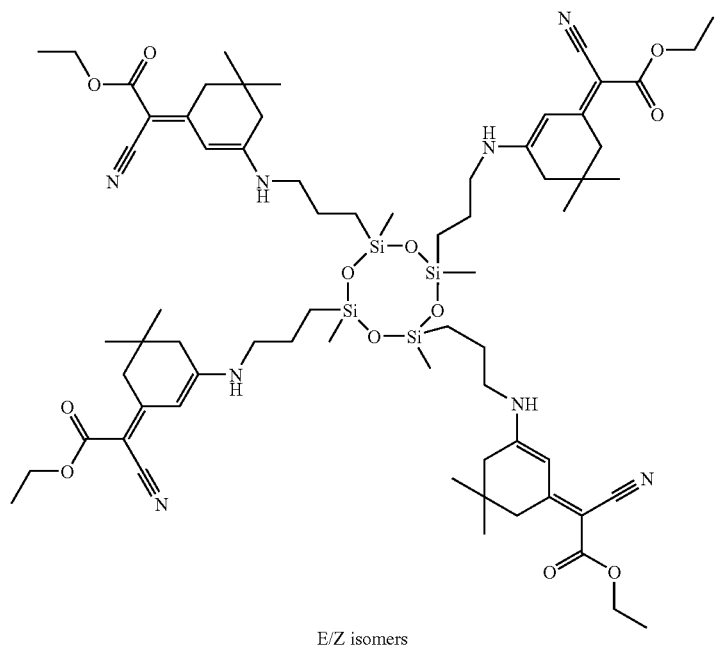 [SMILES: CCOC(=O)/C(C#N)=C1/C=C(NCCC[Si]2(C)O[Si](C)(CCCNC3=C/C(=C(\C#N)C(=O)OCC)CC(C)(C)C3)O[Si](C)(CCCNC3=C/C(=C(\C#N)C(=O)OCC)CC(C)(C)C3)O[Si](C)(CCCNC3=C/C(=C(\C#N)C(=O)OCC)CC(C)(C)C3)O2)CC(C)(C)C1]
E/Z isomers TABLE 1-continued
MC 12
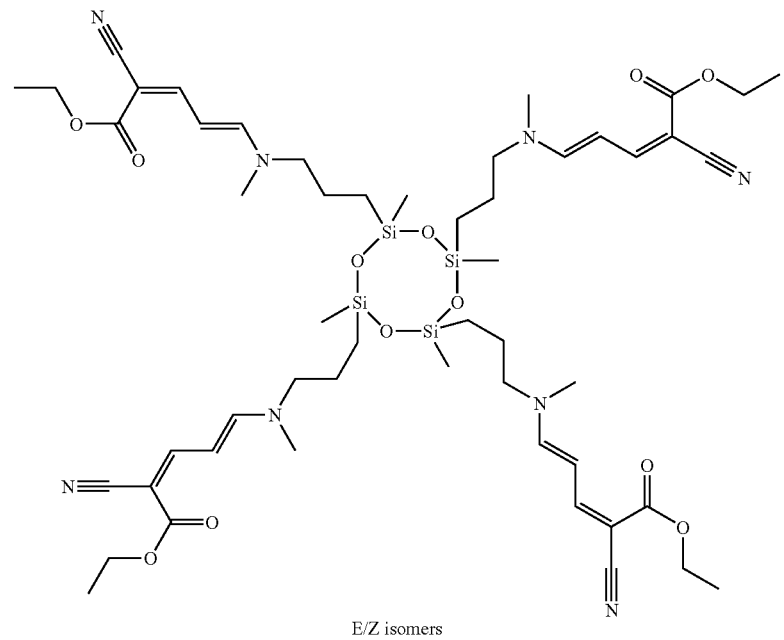 [SMILES: CCOC(=O)/C(C#N)=C\C=C\N(C)CCC[Si]1(C)O[Si](C)(CCCN(C)/C=C/C=C(/C#N)C(=O)OCC)O[Si](C)(CCCN(C)/C=C/C=C(/C#N)C(=O)OCC)O[Si](C)(CCCN(C)/C=C/C=C(/C#N)C(=O)OCC)O1]
E/Z isomers
MC 13
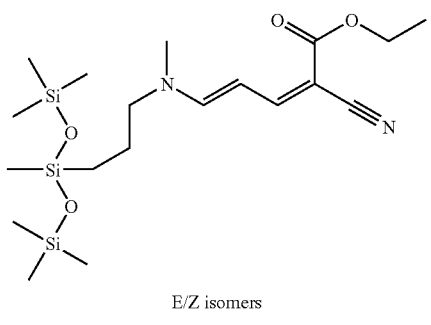 [SMILES: CCOC(=O)/C(C#N)=C\C=C\N(C)CCC[Si](C)(O[Si](C)(C)C)O[Si](C)(C)C]
E/Z isomers
MC 14
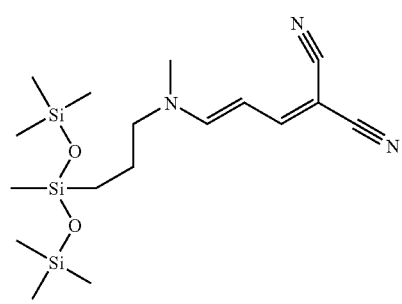 [SMILES: CN(/C=C/C=C(C#N)C#N)CCC[Si](C)(O[Si](C)(C)C)O[Si](C)(C)C]

TABLE 1-continued
MC 15
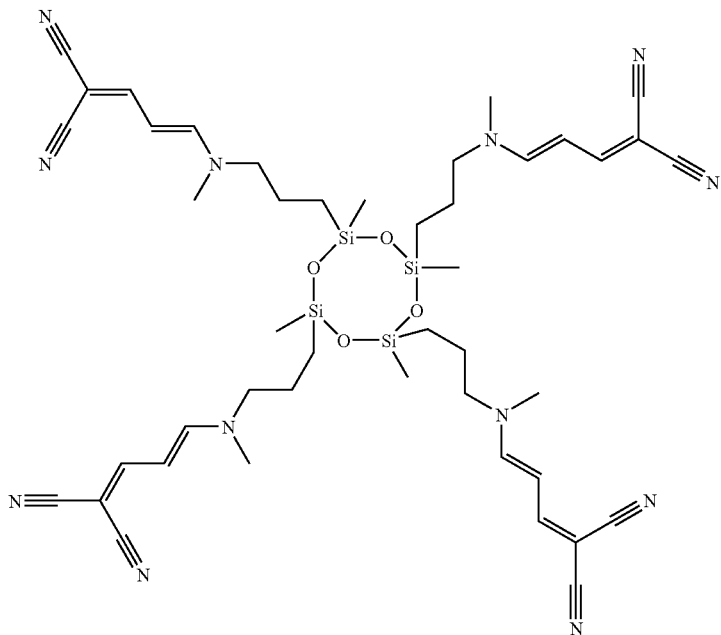 [SMILES: CN(/C=C/C=C(C#N)C#N)CCC[Si]1(C)O[Si](C)(CCCN(C)/C=C/C=C(C#N)C#N)O[Si](C)(CCCN(C)/C=C/C=C(C#N)C#N)O[Si](C)(CCCN(C)/C=C/C=C(C#N)C#N)O1]
MC 16
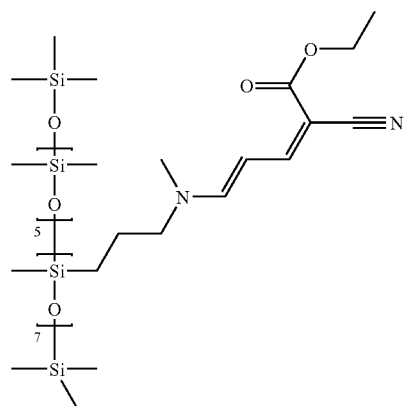
E/Z isomers
MC 17
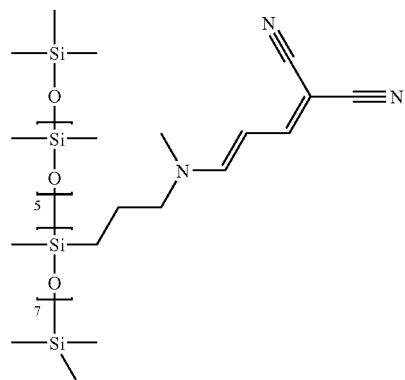

TABLE 1-continued
MC 18
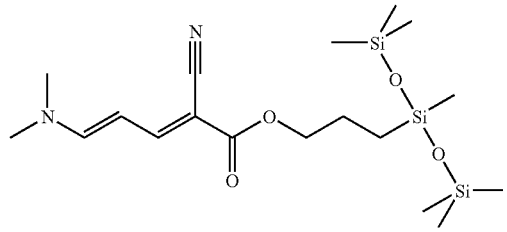
MC 19
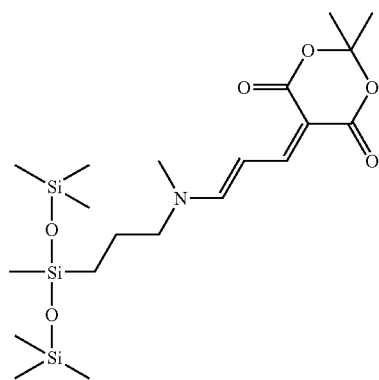
MC 20
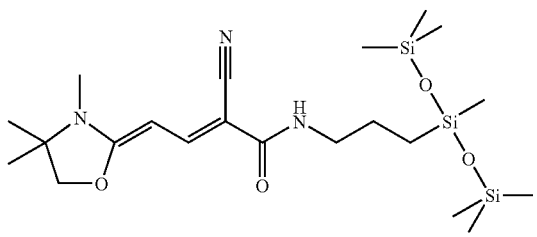
MC 21
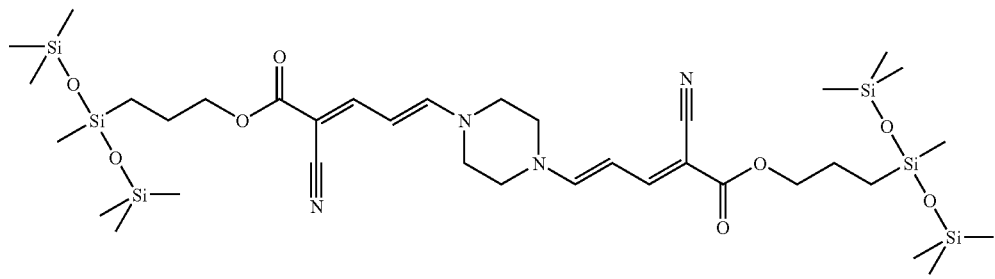
* =
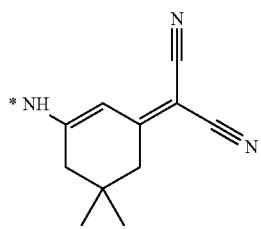

The compounds according to this invention can be prepared as follows:

In a first step compounds of the general formula (1) are synthesized in which one of the groups $R_1$, $R_2$, $R_3$ or $R_4$ are defined as above and containing an unsaturated C—C bond which can be subsequently hydrosilylated. In the next step the reaction between the unsaturated compound and a SiH containing silane, oligosiloxane and polysiloxane is performed in the presence of a hydrosilylation catalyst. The following reaction scheme exemplifies the hydrosilylation reactions.

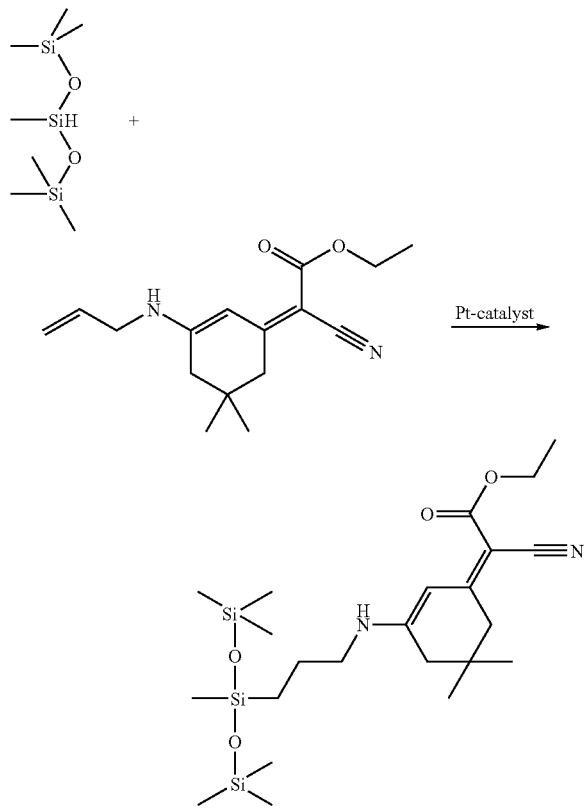

An example for a transesterification reaction is given below for the reaction between a carboxylic acid ester and an alcohol containing an organo siloxane group. In the following scheme the groups $R_1$, $R_2$, $R_3$, $R_4$, $L_1$, $L_2$ or $L_3$ are defined as described above.

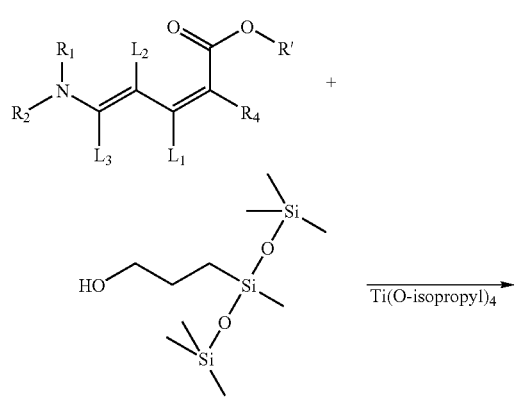

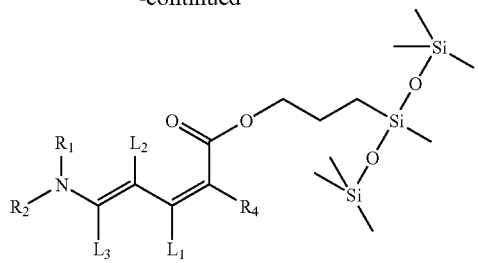

The merocyanine precursors which are described in the two reaction schemes above can be prepared according to known procedures as described in several patent applications like for example U.S. Pat. No. 4,045,229, U.S. Pat. No. 4,195,999, WO 0020388, U.S. Pat. No. 4,455,368, U.S. Pat. No. 4,309,500 or WO 04/006878.

The compounds of the formula (1) according to the present invention are particularly suitable as UV filters, i.e. for protecting ultraviolet-sensitive organic materials, in particular the skin and hair of humans and animals, from the harmful effects of UV radiation. These compounds are therefore suitable as sunscreens in cosmetic, pharmaceutical and veterinary medical preparations. These compounds can be used both in dissolved form and in the micronized state.

The cosmetic formulations or pharmaceutical compositions according to the present invention may additionally contain one or more than one further UV filter as listed in Table 3.

TABLE 2

Suitable UV filter substances which can be additionally used with the UV absorbers according to the present invention

| | |
|---|---|
| DE 10013318 | T 1 pp 8-9, all Examples pp 10-13, T 2 pp 13-14, all Examples p 14, Ex A, B, C, D, E, F pp 19-20 |
| DE 10206562 A1 | Ex 1-3 p 10, Ex 4-7 p 11, Ex 8-15 pp 12-14 |
| DE 10238144 A1 | Ex on p 3-5; |
| DE 10331804 | T 1 p 4, T 2 + 3 p 5 |
| DE 19704990 A1 | Ex 1-2 on pp 6-7; |
| EP 613 893 | Ex 1-5 + 15, T 1, pp 6-8 |
| EP 0 998 900 A1 | Ex on pp 4-11 |
| EP 1 000 950 | Comp. In Table 1, pp 18-21 |
| EP 1 005 855 | T 3, p 13 |
| EP 1 008 586 | Ex 1-3, pp 13-15 |
| EP 1 008 593 | Ex 1-8, pp 4-5 |
| EP 1 027 883 | Compound VII, p 3 |
| EP 1 027 883 | Comp I-VI, p 3 |
| EP 1 028 120 | Ex 1-5, pp 5-13 |
| EP 1 059 082 | Ex 1; T 1, pp 9-11 |
| EP 1 060 734 | T 1-3, pp 11-14 |
| EP 1 064 922 | Compounds 1-34, pp 6-14 |
| EP 1 077 246 A2 | Ex 1-16 on pp 5-11; |
| EP 1 081 140 | Ex 1-9, pp 11-16 |
| EP 1 103 549 | Compounds 1-76, pp 39-51 |
| EP 1 108 712 | 4,5-Dimorph olino-3-hydroxypyridazine |
| EP 1 123 934 | T 3, p 10 |
| EP 1 129 695 | Ex 1-7, pp 13-14 |
| EP 1 167 359 | Ex 1, p 11 and Ex 2, p 12 |
| EP 1 232 148 B1 | Ex 4-17 on pp 3-5; |
| EP 1 258 481 | Ex 1, pp 7, 8 |
| EP 1 310 492 A1 | Ex 1-16 on pp 22-30 |
| EP 1 371 654 A1 | Ex on pp 5-7 |
| EP 1 380 583 A2 | Ex 1, p 6; |
| EP 1 423 351 A2 | Ex 1-16 on pp 31-37; |
| EP 1 423 371 A1 | T 1 on pp 4-8, Ex on p 9, Ex 1-9 on pp 36-42; |
| EP 1 454 896 A1 | Ex 1-5 on pp 10-13, Examples on pp 4-5; |
| EP 1 471 059 A1 | Ex 1-5 on pp 4-5; |
| EP 1484051 A2 | Formula III-VII on pp18-19, Ex 7-14 on pp 7-9, Ex 18-23 on pp 11-12, Ex 24-40 on pp 14-17; |
| EP 420 707 B1 | Ex 3, p 13 (CAS Reg. No 80142-49-0) |

TABLE 2-continued

Suitable UV filter substances which can be additionally used with the UV absorbers according to the present invention

| | |
|---|---|
| EP 503 338 | T 1, pp 9-10 |
| EP 517 103 | Ex 3, 4, 9, 10 pp 6-7 |
| EP 517 104 | Ex 1, T 1, pp 4-5; Ex 8, T 2, pp 6-8 |
| EP 626 950 | all compounds |
| EP 669 323 | Ex 1-3, p 5 |
| EP 743 309 A1 | Ex 1-12 on pp 18-24; |
| EP 780 382 | Ex 1-11, pp 5-7 |
| EP 823 418 | Ex 1-4, pp 7-8 |
| EP 826 361 | T 1, pp 5-6 |
| EP 832 641 | Ex 5 + 6 p 7; T 2, p 8 |
| EP 832 642 | Ex 22, T 3, pp 10-15; T 4, p 16 |
| EP 852 137 | T 2, pp 41-46 |
| EP 858 318 | T 1, p 6 |
| EP 863 145 | Ex 1-11, pp 12-18 |
| EP 878 469 A1 | T 1, pp 5-7; |
| EP 895 776 | Comp. In rows 48-58, p 3; R 25 + 33, p 5 |
| EP 911 020 | T 2, pp 11-12 |
| EP 916 335 | T 2-4, pp 19-41 |
| EP 924 246 | T 2, p 9 |
| EP 933 376 | Ex 1-15, pp 10-21 |
| EP 944 624 | Ex 1 + 2, pp 13-15 |
| EP 945 125 | T 3 a + b, pp 14-15 |
| EP 95 097 | Ex 1, p 4 |
| EP 967 200 | Ex 2; T 3-5, pp 17-20 |
| EP 969 004 | Ex 5, T 1, pp 6-8 |
| FR 2842806 A1 | Ex I p 10, Ex II p 12 |
| FR 2861075 A1 | Ex 1-3 on pp 12-14; |
| FR 2862641 | Formula 3 on p4; Ex A-J on pp 7-9; |
| KR 2004025954 | all kojyl benzoate derivatives |
| JP 06135985 A2 | Formula 1 on p 2; Ex 1-8 on pp 7-8; |
| JP 2000319629 | CAS Reg Nos. 80142-49-0, 137215-83-9, 307947-82-6 |
| JP 2003081910 A | Ex on p 1; |
| JP 3686911 B2 | All benzylidene-gamma-butyrolactone derivatives |
| US 2003/0053966A1 | Ex on pp 3-6 |
| US 2004057912 A1 | Ex on p 7-9, Ex 1 on p 10; |
| US 2004057914 A1 | Ex on p 8-12, Ex 1 on p 12; |
| US 2004/0057911A1 | Formula I and II on p 1; formula III and IV on p3; Ex 1-3 on pp 5-6; |
| US 2004/0071640A1 | Ex 1-12 on pp 4-7; |
| US 2004/0091433A1 | Ex 1-6 on pp 14-16; |
| US 2004/0136931A1 | Ex 1-3 on p 7; |
| US 2004/0258636A1 | Ex 1-11 on pp 9-15; |
| US 2005/0019278A1 | Ex 1-9 on pp 6-8; |
| US 2005/0136012A1 | Formula 1 on p 2; |
| US 2005/0136014A1 | Formula a-c on p 2; Examples on p 3; |
| US 2005/0201957A1 | Formula 1 on p1; Ex A, B, C, D, E, F, G on pp 2-3; |
| US 2005/0249681A1 | all compounds on pp 2-3, Ex 1 on p 6; |
| US 5 635 343 | all compounds on pp 5-10 |
| US 5 332 568 | Ex 1, p 5, T 1 + 2, pp 6-8 |
| US 5 338 539 | Ex 1-9, pp 3 + 4 |
| US 5 346 691 | Ex 40, p 7; T 5, p 8 |
| US 5 801 244 | Ex 1-5, pp 6-7 |
| US 6613340 | Ex I, II pp 9-11, Examples on rows 28-53 p 6 |
| US 6 800 274 B2 | Formulas I-VI and IX-XII on pp 14-18; |
| US 6 890 520 B2 | Ex 1-10 on pp 6-9; |
| US 6926887 B2 | Ex A on pp5/6; Formulas I-VIII on pp 27-29; |
| US 6936735 B2 | Formula 1-2 on p 2; formula 3-4 on p 6; |
| WO 0149686 | Ex 1-5, pp 16-21 |
| WO 0168047 | Tables on pp 85-96 |
| WO 0181297 | Ex 1-3, pp 9-11 |
| WO 0191695 | Formula I on p 4, T on p 8 |
| WO 0202501 A1 | Ex Ia-c, p 5 |
| WO 02069926 A1 | Ex on p 9, Ex on pp 17-23 |
| WO 02072583 | T on pp 68-70 |
| WO 02080876 | Ex 1 on pp 7-9 |
| WO 0238537 | All compounds p 3, compounds on rows 1-10 p 4 |
| WO 03004557 A1 | Ex A1-A29 on pp 36-57; |
| WO 03007906 | Ex I-XXIII, pp 42-48 |
| WO 03086341 A2 | Formula 2-21, pp 4-6; |
| WO 03092643 A1 | T on pp 34-35, compounds listed on p 16 |
| WO 03097577 A1 | Ex on pp 6-8; Ex 1-3 on pp 15-18; |
| WO 03104183 A1 | Formula I-IV on p 1; Ex 1-5 on pp 27-28; |
| WO 04000256 A1 | Ex 1-10 on pp 18-24 |
| WO 04020398 A1 | Ex 1-3 on pp 14-17 |
| WO 04020398 A1 | Formulas I-VI on pp 21-24, Formula IX on p 25; |
| WO 05009938 A2 | Formula I on p 1; Ex 1-2 on pp 14-15; |
| WO 05065154 A2 | Formula a-c on pp 5-6; |
| WO 05080341 A1 | Formula 1 on p 3; Examples on pp 9-13; |
| WO 9217461 | Ex 1-22, pp 10-20 |
| WO 9220690 | Polymeric Comp in Examples 3-6 |
| WO 9301164 | T 1 + 2, pp 13-22 |
| WO 9714680 | Ex 1-3, p 10 |

(Abbreviations T: Table, R: row, Comp: compound, Ex: compound(s) of Patent Example, p: page; the generic scope of the UV absorbers is described in the left-hand column; specific compounds are indicated in the right-hand column)

The cosmetic or pharmaceutical preparations can be prepared by physically mixing the UV absorber(s) with the adjuvant using customary methods, for example by simply stirring together the individual components, especially by making use of the dissolution properties of already known cosmetic UV absorbers, like octyl methoxy cinnamate, salicylic acid isooctyl ester, etc. The UV absorber can be used, for example, without further treatment, or in the micronised state, or in the form of a powder.

Cosmetic or pharmaceutical preparations contain from 0.05-40% by weight, based on the total weight of the composition, of one UV absorber or UV absorber mixtures.

Preference is given to the use of mixing ratios of the UV absorber of formula (1) according to the present invention and optionally further light-protective agents (as described in Table 2) from 1:99 to 99:1, preferably from 1:95 to 95:1 and most preferably from 10:90 to 90:10, based on weight. Of special interest are mixing ratios of from 20:80 to 80:20, preferably from 40:60 to 60:40 and most preferably approximately 50:50. Such mixtures can be used, inter alia, to improve the solubility or to increase UV absorption.

The UV absorbers of formula (1) according to the present invention or combinations of UV filters are useful to protect skin, hair and/or natural or artificial hair color.

The cosmetic or pharmaceutical preparations may be, for example, creams, gels, lotions, alcoholic and aqueous/alcoholic solutions, emulsions, wax/fat compositions, stick preparations, powders or ointments. In addition to the above mentioned UV filters, the cosmetic or pharmaceutical preparations may contain further adjuvants as described below.

As water- and oil-containing emulsions (e.g. W/O, O/W, O/W/O and W/O/W emulsions or microemulsions) the preparations contain, for example, from 0.1 to 30% by weight, preferably from 0.1 to 15% by weight and especially from 0.5 to 10% by weight, based on the total weight of the composition, of one or more UV absorbers, from 1 to 60% by weight, especially from 5 to 50% by weight and preferably from 10 to 35% by weight, based on the total weight of the composition, of at least one oil component, from 0 to 30% by weight, especially from 1 to 30% by weight und preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically acceptable adjuvants.

The cosmetic or pharmaceutical compositions/preparations according to the invention may also contain one or one more additional compounds like fatty alcohols, esters of fatty acids, natural or synthetic triglycerides including glyceryl esters and derivatives, pearlescent waxes, hydrocarbon oils, silicones or siloxanes (organosubstituted polysiloxanes), fluorinated or perfluorinated oils, emulsifiers, super-fatting agents, surfactants, consistency regulators/thickeners and rheology modifiers, polymers, biogenic active ingredients, deodorising active ingredients, anti-dandruff agents, antioxidants, hydrotropic agents, preservatives and bacteria-inhibiting agents, perfume oils, colourants, polymeric beads or hollow spheres as SPF enhancers.

Cosmetic or Pharmaceutical Preparations

Cosmetic or pharmaceutical formulations are contained in a wide variety of cosmetic preparations. There come into consideration, for example, especially the following preparations:

- skin-care preparations, e.g. skin-washing and cleansing preparations in the form of tablet-form or liquid soaps, soapless detergents or washing pastes,
- bath preparations, e.g. liquid (foam baths, milks, shower preparations) or solid bath preparations, e.g. bath cubes and bath salts;
- skin-care preparations, e.g. skin emulsions, multi-emulsions or skin oils;
- cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;
- foot-care preparations, e.g. foot baths, foot powders, foot creams or foot balsams, special deodorants and antiperspirants or callus-removing preparations;
- light-protective preparations, such as sun milks, lotions, creams or oils, sunblocks or tropicals, pre-tanning preparations or after-sun preparations;
- skin-tanning preparations, e.g. self-tanning creams;
- depigmenting preparations, e.g. preparations for bleaching the skin or skin-lightening preparations;
- insect-repellents, e.g. insect-repellent oils, lotions, sprays or sticks;
- deodorants, such as deodorant sprays, pump-action sprays, deodorant gels, sticks or roll-ons;
- antiperspirants, e.g. antiperspirant sticks, creams or roll-ons;
- preparations for cleansing and caring for blemished skin, e.g. synthetic detergents (solid or liquid), peeling or scrub preparations or peeling masks;
- hair-removal preparations in chemical form (depilation), e.g. hair-removing powders, liquid hair-removing preparations, cream- or paste-form hair-removing preparations, hair-removing preparations in gel form or aerosol foams;
- shaving preparations, e.g. shaving soap, foaming shaving creams, non-foaming shaving creams, foams and gels, preshave preparations for dry shaving, aftershaves or aftershave lotions;
- fragrance preparations, e.g. fragrances (eau de Cologne, eau de toilette, eau de parfum, parfum de toilette, perfume), perfume oils or perfume creams;
- cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hairfoams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

Presentation Forms

The final formulations listed may exist in a wide variety of presentation forms, for example:

- in the form of liquid preparations as a W/O, O/W, O/W/O, W/O/W or PIT emulsion and all kinds of microemulsions,
- in the form of a gel,
- in the form of an oil, a cream, milk or lotion,
- in the form of a powder, a lacquer, a tablet or make-up,
- in the form of a stick,
- in the form of a spray (spray with propellent gas or pump-action spray) or an aerosol,
- in the form of a foam, or
- in the form of a paste.

Of special importance as cosmetic preparations for the skin are light-protective preparations, such as sun milks, lotions, creams, oils, sunblocks or tropicals, pretanning preparations or after-sun preparations, also skin-tanning preparations, for example self-tanning creams. Of particular interest are sun protection creams, sun protection lotions, sun protection milk and sun protection preparations in the form of a spray.

Of special importance as cosmetic preparations for the hair are the above-mentioned preparations for hair treatment, especially hair-washing preparations in the form of shampoos, hair conditioners, hair-care preparations, e.g. pretreatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition: from 0.01 to 5% by weight of a UV absorber according to the invention, 12.0% by weight of sodium laureth-2-sulfate, 4.0% by weight of cocamidopropyl betaine, 3.0% by weight of sodium chloride, and water ad 100%.

The cosmetic preparation according to the invention is distinguished by excellent protection of human skin against the damaging effect of sunlight.

The following examples illustrate the invention in more detail, but do not limit its scope in any manner.

A. Preparation Examples

Example A1

Preparation of MC 07

1.87 g (0.008 mol, 95%) of 1,1,1,3,5,5,5-heptamethyltrisiloxane are added to a mixture of 1.82 g (0.008 mol) of 2-(3-allylamino-5,5-dimethyl-cyclohex-2-enylidene)-malononitrile and 10 μl of platinum(0)-1,3-divinyl-1,1,3,3-tetramethyldisiloxane complex (soln. in poly (dimethylsiloxane, vinyl terminated, purchased from the company Aldrich) dissolved in 6 ml of xylene at 65° C. Heating is continued at 140° C. for 18 h. Then another 1.87 g (0.008 mol, 95%) of 1,1,1,3,5,5,5-heptamethyltrisiloxane and 5 drops of the catalytic solution are added. Heating is continued at 110° C. for 30 h. After concentrating the residue is taken up in a hot 1/1 ethanol/toluene mixture. After adding charcoal the mixture is stirred at 80° C. for 1 h. The solid is filtered off and washed with a little amount of a 1/1 ethanol/toluene mixture. The filtrate is concentrated under vacuo and dried at 70-80° C.

2.99 g (83% yield) of a pasty residue are obtained which solidifies to an orangebrown resin. UV (CH$_3$CN/H$_2$O): $\lambda_{max}$=382 nm; UV(EtOH): $\lambda_{max}$=381 nm; $\epsilon$=52829.

Example A2

Preparation of MC 08

1.87 g (0.008 mol, 95%) of 1,1,1,3,5,5,5-heptamethyltrisiloxane are added to a mixture of 2.19 g (0.008 mol) of [3-allylamino-5,5-dimethyl-cyclohex-2-en-(Z)-ylidene]-cyano-acetic acid ethyl ester and 10 μl of platinum(0)-1,3-divinyl-1,1,3,3-tetramethyldisiloxane complex (soln. in poly(dimethylsiloxane, vinyl terminated, from Aldrich) dissolved in 6 ml of toluene at 65° C. Heating is continued at 95° C. for 18 h. After concentrating the residue is taken up in a hot 1/1 ethanol/toluene mixture. After adding charcoal the mixture is stirred at 80° C. for 1 h. The solid is filtered off and washed with a little amount of a 1/1 ethanol/toluene mixture. The filtrate is concentrated under vacuo and dried at 70-80° C.

3.34 g (84% yield) of an orange resin are obtained. UV (EtOH): $\lambda_{max}$=388 nm, $\epsilon$=50383.

Example A3

Preparation of MC 13

0.88 g (0.004 mol) of (2Z,4E)-5-(allyl-methyl-amino)-2-cyano-penta-2,4-dienoic acid ethyl ester and 5 drops of platinum(0)-1,3-divinyl-1,1,3,3-tetramethyldisiloxane complex (soln. in poly-(dimethylsiloxane, vinyl terminated, from Aldrich) are mixed in 3 ml xylene and heated up to 65° C. After addition of 1.87 g (0.008 mol, 95%) of 1,1,1,3,5,5,5-heptamethyltrisiloxane heating is continued at 115° C. for 18 h. Then 3 ml of ethanol and charcoal are added and the resulting mixture is stirred at 80° C. for 1 h. The hot mixture is filtered over a silica gel pad which is subsequently washed with xylene and ethyl acetate. The collected eluent is concentrated. The residue is dried at 90° C. at 1×10$^{-3}$ bar for 4 h rendering 0.69 g (39% yield) of the product as an orangebrown resin. UV (CH$_3$CN/H$_2$O): $\lambda_{max}$=381 nm.

UV EtOH: $\lambda_{max}$=380 nm; $\epsilon$=69116.

Example A4

Preparation of MC 14

To a solution of 0.31 g (0.0018 mol) of 2-[(E)-3-(allyl-methyl-amino)-allylidene]-malononitrile and 3 drops of platinum(0)-1,3-divinyl-1,1,3,3-tetramethyldisiloxane complex (soln. in poly-(dimethyl-siloxane, vinyl terminated, from Aldrich) dissolved in 2 ml of xylene are added 0.84 g (0.0036 mol, 95%) of 1,1,1,3,5,5,5-heptamethyltrisiloxane at 60° C. Heating is continued at 115° C. for 18 h. The reaction mixture is diluted with 2 ml ethanol and stirred with charcoal at 80° C. for 1 h. After filtration over a hot silica gel pad and washing the pad with toluene and ethyl acetate the eluent is concentrated in vacuo.

The residue is dried at 90° C. at 1×10$^{-3}$ bar for 4 hours rendering 0.53 g (yield: 74%) of the expected derivative as an orangebrown resin.

UV(CH$_3$CN, H$_2$O): $\lambda_{max}$=383 nm.

Example A5

Preparation of MC 06

1.82 g (0.008 mol) of 2-(3-allylamino-5,5-dimethyl-cyclohex-2-enylidene)-malononitrile and 10 μl platinum(0)-1,3-divinyl-1,1,3,3-tetramethyldisiloxane complex (soln. in poly(dimethylsiloxane, vinyl terminated, from Aldrich) are dissolved in 6 ml toluene at 65° C. 0.49 g (0.002 mol, 99%) 2,4,6,8-tetramethylcyclotetrasiloxane is added and heating is continued at 95° C. for 18 h. After concentrating the residue is dissolved in a hot 1/1 ethanol/toluene mixture. Charcoal is added and the mixture is stirred for 1 h at 80° C. The solid is filtered off. The filtrate is concentrated to dryness. After drying at 70-80° C. in vacuum 2.05 g (89% yield) of the desired product are obtained in form of a dark yellow solid having a melting point of ~100° C.

UV (EtOH): $\lambda_{max}$=381 nm, $\epsilon$=177914;

Example A6

Preparation of MC 11

To a hot solution of 2.19 g (0.008 mol) of [3-allylamino-5,5-dimethyl-cyclohex-2-en-(Z)-yli-dene]-cyano-acetic acid ethyl ester and 10 μl platinum(0)-1,3-divinyl-1,1,3,3-tetramethyldisiloxane complex (soln. in poly(dimethylsiloxane, vinyl terminated, from Aldrich) dissolved in 6 ml toluene is added 0.49 g (0.002 mol, 99%) 2,4,6,8-tetramethylcyclotetrasiloxane. Heating is continued at 95° C. for 18 h. After addition of another 10 μl-quantity of the catalytic system the mixture is heated at 110° C. for 18 h. The mixture is then concentrated to dryness and dissolved in 10 ml of a hot 1/1 ethanol/toluene mixture. The resulting mixture is stirred together with charcoal at 80° C. for 1 h. After filtration the mixture is concentrated and the orange solid residue dried at 70-80° C. in vacuum yielding 2.69 g (100%) of the desired product.

UV (EtOH): $\lambda_{max}$=388 nm, $\epsilon$=181817.

Example A7

Preparation of MC 12

0.88 g (0.004 mol) of (2Z,4E)-5-(allyl-methyl-amino)-2-cyano-penta-2,4-dienoic acid ethyl ester and 5 drops of platinum(0)-1,3-divinyl-1,1,3,3-tetramethyldisiloxane complex (soln. in poly-(dimethylsiloxane, vinyl terminated, from Aldrich) are mixed in hot 3 ml toluene. After addition of 0.24 g (0.001 mol, 99%) of 2,4,6,8-tetramethylcyclotetrasiloxane at 65° C. the reaction mixture is stirred at 115° C. for 18 h. After diluting with 3 ml ethanol and adding charcoal stirring is continued for 1 h at 80° C. The resulting mixture is filtered over a hot silica gel pad, which is washed with small amounts of toluene and ethyl acetate. The eluents are concentrated in vacuum rendering 0.68 g (61% yield) of the product in form of a redbrown resin.

UV (CH$_3$CN, H$_2$O): $\lambda_{max}$=381 nm.

Example A8

Preparation of MC 15

A solution of 0.35 g (0.002 mol) 2-[-3-(allyl-methyl-amino)-allylidene]-malononitrile and 3 drops platinum(0)-1,3-divinyl-1,1,3,3-tetramethyldisiloxane complex (soln. in poly(dimethylsiloxane, vinyl terminated, from Aldrich) dissolved in 2 ml of xylene is heated to 60° C. After addition of 0.12 g (0.0005 mol, 99%) of 2,4,6,8-tetramethylcyclotetrasiloxane heating is continued at 115° C. for 18 h. Another 3 drops of the catalyst solution are added and stirring is continued at 115° C. for 18 h. The reaction mixture is diluted with 2 ml ethanol and stirred with charcoal at 80° C. for 1 h. The hot mixture is then filtered over a hot silica gel pad which is subsequently washed with xylene and ethyl acetate. The eluents are concentrated and residue dried at 90° C. in vacuum for 4 h yielding 0.24 g (51%) of the desired product as an orange resin.

UV ($CH_3CN$, $H_2O$): $\lambda_{max}$=378 nm.

Example A9

Preparation of MC 09

1.82 g (0.008 mol) of 2-(3-allylamino-5,5-dimethyl-cyclohex-2-enylidene)-malononitrile are dissolved together with 10 μl of platinum(0)-1,3-divinyl-1,1,3,3-tetramethyldisiloxane complex (soln. in poly(dimethylsiloxane, vinyl terminated, from Aldrich) in 6 ml xylene. The mixture is heated up to 65° C. and 1.99 g poly(dimethylsiloxane-co-methylhydrosilane) (trimethylsilyl terminated, Mw=950 Dalton, 50 mol % MeHSiO, from Aldrich) are added. Heating is continued at 95° C. for 18 h and then worked up according to the procedure of example 8 yielding 5 g (99%) of the desired derivative as a yellow, pasty resin.

UV (EtOH): $\lambda_{max}$=381 nm; $\epsilon$=165712.

Example A10

Preparation of MC 10

2.01 g poly(dimethylsiloxane-co-methylhydrosilane) (trimethylsilyl terminated, Mw=950 Dalton, 50 mol % MeHSiO, from Aldrich) are added to a hot solution of 2.19 g (0.008 mol) [3-allylamino-5,5-dimethyl-cyclohex-2-en-(Z)-ylidene]-cyano-acetic acid ethyl ester and 10 μl platinum(0)-1,3-divinyl-1,1,3,3-tetramethyldisiloxane complex (soln. in poly(dimethylsiloxane, vinyl terminated, from Aldrich) dissolved in 6 ml xylene. The mixture is stirred at 95° C. for 18 h. After addition of another 10 ml of catalyst solution heating is continued at 110° C. for 18 h. The reaction mixture is then concentrated and worked up according to the procedure described in example 8 rendering 4.7 g (yield: 82%) of the desired product in form of an orange pasty resin.

UV (EtOH): $\lambda_{max}$=388 nm; $\epsilon$=189103.

Example A11

Preparation of MC 16

0.88 g (0.004 mol) of (2Z,4E)-5-(allyl-methyl-amino)-2-cyano-penta-2,4-dienoic acid ethyl ester and 5 drops of platinum(0)-1,3-divinyl-1,1,3,3-tetramethyldisiloxane complex (soln. in poly-(dimethylsiloxane, vinyl terminated, from Aldrich) are mixed in 6 ml xylene at 65° C. After addition of 0.99 g of poly(dimethylsiloxane-co-methylhydrosilane) (trimethylsilyl terminated, Mw=950 Dalton, 50 mol % MeHSiO, from Aldrich) at 65° C. the reaction mixture is stirred at 115° C. for 18 h. After dilution with 6 ml ethanol the reaction mixture is worked up as described in example 7. 0.98 g (yield: 39%) of the expected product are obtained in form of a brownish pasty resin. UV ($CH_3CN$, $H_2O$): $\lambda_{max}$=382 nm.

Example A12

Preparation of MC 17

A solution of 0.35 g (0.002 mol) 2-[-3-(allyl-methyl-amino)-allylidene]-malononitrile and 3 drops of platinum(0)-1,3-divinyl-1,1,3,3-tetramethyldisiloxane complex (soln. in poly(dimethylsiloxane, vinyl terminated, from Aldrich) dissolved in 2 ml xylene is heated to 60° C. After addition of 0.50 g poly(dimethylsiloxane-co-methylhydrosilane) (trimethylsilyl terminated, Mw=950 Dalton, 50 mol % MeHSiO, from Aldrich) at 65° C. the reaction mixture is stirred at 115° C. for 18 h. The mixture is then diluted with 2 ml ethanol and worked up according to the procedure as described in example 8.

The product (0.47 g) is yielded in 43% in form of a brownish resin.

UV ($CH_3CN$, $H_2O$): $\lambda_{max}$=377 nm.

B. Application Examples

| | Examples B1-B5: High protection sunscreens | | | | |
|---|---|---|---|---|---|
| INCI-Name | B1 % w/w | B2 % w/w | B3 % w/w | B4 % w/w | B5 % w/w |
| Synthetic Beeswax | 0.5 | 0.5 | 0.5 | 0.5 | 0.5 |
| Ethylhexyl Methoxycinnamate | 9.8 | 9.8 | 9.8 | 9.8 | 9.8 |
| Isoamyl p-Methoxycinnamate | 2.0 | 2.0 | 2.0 | 2.0 | 2.0 |
| Ethylhexyl Salicylate | 5.0 | 5.0 | 5.0 | 5.0 | 5.0 |
| Butyl Methoxydibenzoylmethane | 4.0 | 4.0 | 3.0 | 4.0 | 3.0 |
| 4-Methylbenzylidene Camphor | 4.0 | 4.0 | 4.0 | 4.0 | 4.0 |
| Bis-Ethylhexyloxyphenol Methoxyphenyl Triazine | 1.0 | 1.0 | 1.0 | 1.0 | 1.0 |
| Cyclopentasiloxane (and) Acrylates/Polytrimethylsiloxymethacrylate Copolymer | 7.0 | | | | |
| Isododecane (and) Acrylates/Polytrimethylsiloxymethacrylate Copolymer | | 8.0 | | | |
| Poly(Glycol Adipate)/Bis-Hydroxyethyoxypropyl Dimethicone Copolymer | | | 5.0 | | |
| Dimethicone | 4.5 | 4.5 | 4.5 | 4.5 | 4.5 |
| C20-22 Alkyl Phosphate (and) C20-22 Alcohols | | 3.0 | | | |
| Candelilla/Jojoba/Rice Bran Polyglyceryl-3 esters (and) glyceryl stearate (and) Cetearyl alcohol (and) Sodium stearoyl lactylate | | | 4.0 | | |
| Glyceryl oleate citrate (and) Caprylic/Capric Triglycerides | | | | 6.0 | |
| Cetearyl Alcohol (and) Dicetyl Phosphate (and) Ceteth-10 Phosphate | 4.5 | | | | 4.5 |
| Cetyl Ricinoleate | 3.0 | 3.0 | 3.0 | 3.0 | 3.0 |

-continued

| INCI-Name | Examples B1-B5: High protection sunscreens | | | | |
|---|---|---|---|---|---|
| | B1 % w/w | B2 % w/w | B3 % w/w | B4 % w/w | B5 % w/w |
| Pentaerythrityl Distearate | | | 3.0 | | 5.0 |
| Glyceryl Dibehenate (and) Tribehenin (and) Glyceryl Behenate | 4.0 | | | | |
| Hydroxypropyl Dimethicone Behenate | | 2.2 | 0.5 | 2.2 | |
| Decyl Cocoate | 1.0 | 1.0 | 1.0 | 1.0 | 1.0 |
| Aqua | Qs to 100 | Qs to 100 | Qs to 100 | Qs to 100 | Qs to 100 |
| Propylene Glycol | 3.0 | 3.0 | 3.0 | 3.0 | 3.0 |
| Methylene Bis-Benzotriazolyl Tetramethylbutylphenol (and) Aqua (and) Decyl Glucoside (and) Propylene Glycol (and) Xanthan Gum | 5.0 | 10.0 | 10.0 | 5.0 | 10.0 |
| Decyl Glucoside | 0.5 | 0.5 | 0.5 | 0.5 | 0.5 |
| Acrylates/Vinyl Neodecanoate Crosspolymer | 0.3 | | | | |
| Ammonium Acryloyldimethyltaurate/VP Copolymer | | 0.3 | 0.3 | 0.3 | 0.3 |
| PVP/dimethylconylacrylate/polycarbamyl/polyglycol ester | | | | | 10.0 |
| Polyester-5 | | | | 3.0 | |
| Phenylbenzimidazole Sulfonic Acid | 2.0 | 2.0 | 2.0 | 2.0 | 2.0 |
| Disteareth-75 IPDI | | | | | 3.0 |
| Disteareth-100 IPDI | 3.0 | | | | |
| Acrylates/Vinyl Neodecanoate Crosspolymer | | 1.5 | 5.0 | 8.0 | |
| Acrylates/C10-30 Alkyl Acrylate Crosspolymer | | | | | 0.2 |
| Disodium EDTA | 0.2 | 0.2 | 0.2 | 0.2 | 0.2 |
| Tromethamine | 0.8 | 0.8 | 0.8 | 0.8 | 0.8 |
| Cyclohexasiloxane (and) Cyclopentasiloxane | 0.8 | 0.8 | 0.8 | 0.8 | 0.8 |
| Phenoxyethanol (and) Methylparaben (and) Ethylparaben (and) Butylparaben (and) Propylparaben (and) Isobutylparaben | 0.8 | 0.8 | 0.8 | 0.8 | 0.8 |
| Tocopheryl Acetate | 0.4 | 0.4 | 0.4 | 0.4 | 0.4 |
| CAS-Regno. 88122-99-0. Ethylhexyl triazone (Octyl triazone; Uvinul T 150) | 1.0 | | | 3.0 | |
| CAS-Regno.6197-30-4. Octocrylene | | 1.0 | 5.0 | | |
| CAS-Regno. 180898-37-7. Disodium phenyldibenzimidazoletetrasulfonate Neo Heliopan AP or Neo-Heliopan APC | | | | | 2.0 |
| CAS-Regno. 68890-66-4. Octopirox | 1.0 | | | | |
| Tinogard TT (INCI Tetradibutyl Pentaerithrityl Hydroxyhydrocinnamate) | 3.0 | | | | 1.0 |
| Tinogard HS (INCI Sodium Benzotriazolyl Butylphenol Sulfonate) | | 3.0 | | | |
| Tinogard TL (INCI Benzotriazolyl Dodecyl p-Cresol) | 0.9 | 1.0 | 3.0 | 0.5 | 1.0 |
| Merocyanine of structure MC08 | 0.3 | 1.0 | 1.0 | 0.5 | 0.3 |
| Cibafast H Liquid (INCI Sodium Benzotriazolyl Butylphenol Sulfonate. Buteth-3. Tributyl Citrate) | | | 1.0 | | |
| Tinogard AS (INCI Bumetrizole) | | | | 1.0 | 1.0 |
| Tris(tetramethylhydroxypiperidinol) citrate (Tinogard Q) | | | | 1.0 | 1.0 |
| 220410-74-2 4-Piperidinol. 1-hydroxy-2.2.6.6-tetramethyl-. 2-hydroxy-1.2.3-propanetricarboxylate (3:1) (salt) | | | 1.0 | | |
| CAS-Regno. 1750-49-8. N-(2-Hydroxypropyl)urea | | 10.0 | | | |
| CAS-Regno. 2078-71-9. N-(2-Hydroxyethyl)urea | 10.0 | | | | |
| mixture of n-butylphthalimide and isopropylphthalimide | | | | | 3.0 |

The invention claimed is:

1. Merocyanine derivatives of formula (1)

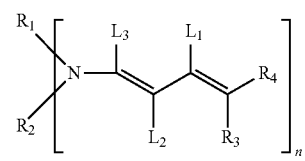
(1)

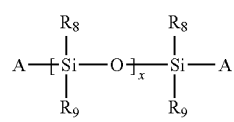
(4a)

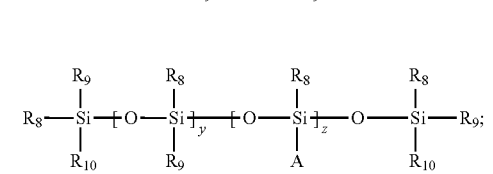
(4b)

wherein $L_2$ is hydrogen; and $L_1$ and $L_3$ are linked together to form a carbocyclic ring;

$R_3$ is $-X_2-Sil_2$, wherein $Sil_2$ is a polysiloxane of the formula (4a) or (4b)

and $X_2$ is $C_1-C_{18}$alkylene; or a bivalent radical of the formula (5a), (5b) or (5c)

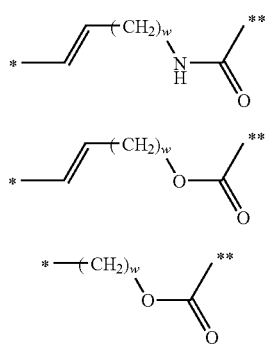

(5a), (5b), (5c)

wherein the asterix * is linked to $Sil_2$ and the asterix ** is linked to $R_3$ or $R_4$; and w is a number from 0 to 30, wherein $R_8$, $R_9$, $R_{10}$ independently form each other are $C_1$-$C_{22}$alkyl; $C_6$-$C_{20}$aryl; $C_1$-$C_{22}$alkoxy; or O—$C_6$-$C_{20}$aryl;

A is a bond to $X_1$ or $X_2$;

x is a number from 4 to 250;

y is a number from 5 to 250; and z is a number from 1 to 50; and n is 1, 2, or 4;

$R_4$ is CN; —$COR_5$; —$COOR_5$; —$CONR_5R_6$; $C_1$-$C_{22}$alkyl; $C_2$-$C_{22}$alkenyl; $C_2$-$C_{22}$alkinyl; $C_3$-$C_{12}$cycloalkyl; $C_3$-$C_{12}$cycloalkenyl; $C_7$-$C_{20}$aralkyl; $C_1$-$C_{20}$heteroalkyl; $C_3$-$C_{12}$cyclo-heteroalkyl; $C_3$-$C_{18}$heteroaralkyl; $C_6$-$C_{20}$aryl; $C_1$-$C_{12}$alkylcarbonylamino-$C_6$-$C_{20}$aryl; $C_2$-$C_{12}$heteroaryl; or —$X_2$—$Sil_2$;

if n=1, $R_1$ and $R_2$ independently of each other are hydrogen; $C_1$-$C_{22}$ alkyl; hydroxy-$C_1$-$C_{22}$alkyl; $C_2$-$C_{22}$alkenyl; $C_2$-$C_{22}$alkinyl; $C_3$-$C_{12}$cycloalkyl; $C_3$-$C_{12}$cycloalkenyl; $C_7$-$C_{20}$aralkyl; $C_1$-$C_{20}$heteroalkyl; $C_3$-$C_{12}$cycloheteroalkyl; $C_6$-$C_{20}$aryl; $C_3$-$C_{18}$heteroaralkyl; $C_2$-$C_{12}$heteroaryl; —$(CH_2)_u$—$SiR_8R_9R_{10}$; or —$X_1$—$Sil_1$;

if n=2, $R_1$ and $R_2$ are each $C_1$-$C_6$alkylene; or one of $R_1$ and $R_2$ is $C_1$-$C_6$alkylene and the other is as defined for n =1;

if n =4, one of $R_1$ and $R_2$ is a tetravalent radical and the other is as defined as for n =1, wherein the tetravalent radical is

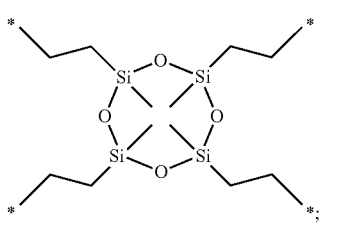

$R_5$ and $R_6$ independently of each other are hydrogen; $C_1$-$C_{22}$alkyl, $C_2$-$C_{22}$alkenyl, $C_2$-$C_{22}$alkinyl; $C_3$-$C_{12}$cycloalkyl; $C_3$-$C_{12}$cycloalkenyl; $C_7$-$C_{20}$aralkyl; $COR_7$; $C_1$-$C_{20}$hetero-alkyl; $C_3$-$C_{12}$cycloheteroalkyl; $C_3$-$C_{18}$heteroaralkyl; $C_6$-$C_{20}$ aryl; $C_1$-$C_5$alkoxy-$C_6$-$C_{20}$aryl; —$(CH_2)_t$—$SO_3H$; —$(CH_2)_v$—(CO)—$OR_7$; —$(CH_2)_t$—O—$C_6$-$C_{10}$aryl; $C_2$-$C_{12}$heteroaryl; —$(CH_2)_u$—$SiR_8R_9R_{10}$; or a radical —$X_2$—$Sil_2$;

$R_7$ is hydrogen; $C_1$-$C_{22}$alkyl; $C_2$-$C_{22}$alkenyl; $C_2$-$C_{22}$alkinyl; $C_3$-$C_{12}$cycloalkyl; $C_3$-$C_{12}$cycloalkenyl; $C_7$-$C_{20}$ aralkyl; $C_1$-$C_{20}$heteroalkyl; $C_3$-$C_{12}$cycloheteroalkyl; $C_3$-$C_{18}$heteroaralkyl; $C_6$-$C_{20}$aryl; or $C_2$-$C_{12}$heteroaryl;

$R_8$, $R_9$, $R_{10}$ independently form each other are $C_1$-$C_{22}$alkyl; $C_6$-$C_{20}$aryl; $C_1$-$C_{22}$alkoxy; or O—$C_6$-$C_{20}$aryl;

and each alkyl, alkenyl, alkinyl, cycloalkyl or cycloalkylene group is unsubstituted or substituted by one or more $R_{12}$;

and each aryl, heteroaryl, aralkyl, arylene, heteroarylene or aralkylene is unsubstituted or substituted by one or more $R_{13}$;

$R_{12}$ is halogen, OH; $NR_{16}R_{17}$; O—$R_{16}$; S—$R_{16}$; CO—$R_{16}$; O—CO—$R_{16}$; oxo; thiono; CN; $COOR_{16}$; $CONR_{16}R_{17}$; $SO_2NR_{16}R_{17}$; $SO_2R_{16}$; $SO_3R_{16}$; $SiR_8R_9R_{10}$; $OSiR_8R_9R_{10}$; $POR_8R_9$; or a radical —$X_3$—$Sil_3$;

$R_{13}$ is $C_1$-$C_{12}$alkylthio; $C_3$-$C_{12}$cycloalkylthio; $C_1$-$C_{12}$alkenylthio; $C_3$-$C_{12}$cycloalkenylthio; $C_1$-$C_{12}$alkoxy; $C_3$-$C_{12}$cycloalkoxy; $C_1$-$C_{12}$alkenyloxy; or $C_3$-$C_{12}$cycloalkenyloxy which is unsubstituted or substituted by one or more $R_{12}$; halogen; CN; SH; OH; CHO; $R_{18}$; $OR_{18}$; $SR_{18}$; $C(R_{18})$=$CR_{19}R_{20}$; O—CO—$R_{19}$; $NR_{18}R_{19}$; $CONR_{18}R_{19}$; $SO_2NR_{18}R_{19}$; $SO_2R_{18}$; $COOR_{18}$, $OCOOR_{18}$; $NR_{19}COR_{20}$; $NR_{19}COOR_{20}$; $SiR_8R_9R_{10}$; $OSiR_8R_9R_{10}$; P(=O)$R_8R_9$; or a radical —$X_4$—$Sil_4$;

$R_{16}$, $R_{17}$, $R_{18}$, $R_{19}$ and $R_{20}$ independently of each other are hydrogen; $C_1$-$C_{22}$alkyl; $C_3$-$C_{12}$cycloalkyl; $C_2$-$C_{12}$alkenyl; $C_3$-$C_{12}$cycloalkenyl; $C_6$-$C_{20}$aryl; $C_2$-$C_{12}$heteroaryl; $C_7$-$C_{18}$aralkyl; or $C_3$-$C_{18}$heteroaralkyl;

$R_{16}$ and $R_{17}$ and/or $R_{18}$ and $R_{19}$ may be linked together to form unsubstituted or $C_1$-$C_4$alkyl-substituted pyrrolidine, piperidine, piperazine or morpholine;

$X_1$, $X_3$ and $X_4$ independently from each other are a linker;

wherein the linker is a divalent radical of formula (5)

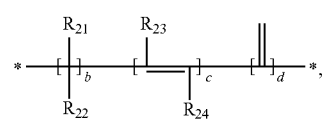

(5)

wherein $R_{21}$, $R_{22}$, $R_{23}$ and $R_{24}$ independently form each other are hydrogen; $C_1$-$C_{22}$alkyl; $C_6$-$C_{20}$aryl; $C_1$-$C_{22}$alkoxy; or O—$C_6$-$C_{20}$aryl;

b is a number from 0 to 30;

c is a number from 0 to 6; and d is a number from 0 to 1;

$Sil_1$, $Sil_3$ and $Sil_4$ independently from each other are a silane-, oligosiloxane or polysiloxane moiety;

t is a number from 0 to 12;

u is a number from 0 to 12; and v is a number from 0 to 12.

2. Merocyanine derivatives according to claim 1, wherein in formula (1)
$L_1$ and $L_3$ together form a bivalent radical selected from

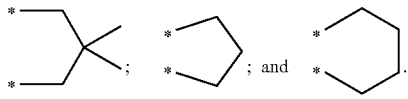

3. Merocyanine derivatives according to claim 1, wherein in formula (1)
$R_1$ is $C_1$-$C_8$alkyl or a radical $X_1$—$Sil_1$,
wherein $X_1$ is $C_1$-$C_3$alkylene; and $Sil_1$ is a radical of formula

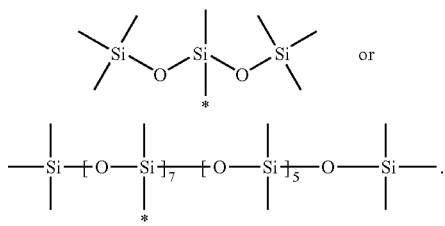

4. Merocyanine derivatives according to claim 1, wherein in formula (1)
$R_2$ is hydrogen; or $C_1$-$C_3$alkyl.

5. Merocyanine derivatives according to claim 1, wherein in formula (1)
$R_3$ is $X_2$—$Sil_2$, wherein $Sil_2$ is

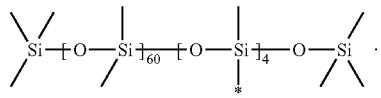

6. Merocyanine derivatives according to claim 1, wherein in formula (1)

$R_4$ is —$COOR_5$; or $C\equiv N$; and
$R_5$ is hydrogen; or $C_1$-$C_{22}$alkyl.

7. Merocyanine derivatives according to claim 5, which correspond to formula (6)

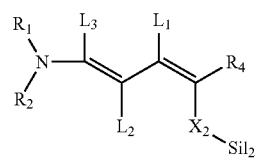

(6)

wherein
$R_1$ and $R_2$ independently from each other are hydrogen; or $C_1$-$C_5$alkyl;
$L_2$ is hydrogen and $L_1$ and $L_3$ form a bivalent radical selected from

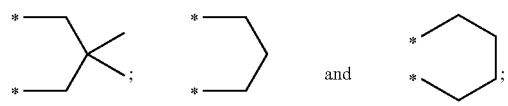

$R_4$ is —$COR_5$;
$R_5$ is $C_1$-$C_5$alkyl;
$Sil_2$ is a radical of formula

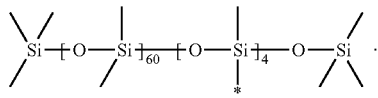

8. Cosmetic composition comprising a merocyanine derivative of formula (1) according to claim 1 and at least one cosmetic acceptable carrier.

* * * * *